US012678099B2

(12) United States Patent
Wingelaar et al.

(10) Patent No.: US 12,678,099 B2
(45) Date of Patent: Jul. 14, 2026

(54) BABY VITAL SIGN MONITORING BELT

(71) Applicant: Bambi Belt Holding B.V., Eindhoven (NL)

(72) Inventors: Paul Jan Hubertus Wingelaar, Eindhoven (NL); Aron Wierts, Eindhoven (NL); Claudia Caparelli, Eindhoven (NL); Karthikeyan Visvanathan, Eindhoven (NL)

(73) Assignee: BAMBI BELT HOLDING B.V., Eindhoven (NL)

( * ) Notice: Subject to any disclaimer, the term of this patent is extended or adjusted under 35 U.S.C. 154(b) by 0 days.

(21) Appl. No.: 18/292,076

(22) PCT Filed: Jul. 25, 2023

(86) PCT No.: PCT/NL2023/050399
§ 371 (c)(1),
(2) Date: Jan. 25, 2024

(87) PCT Pub. No.: WO2024/025416
PCT Pub. Date: Feb. 1, 2024

(65) Prior Publication Data
US 2025/0152102 A1     May 15, 2025

(30) Foreign Application Priority Data
Jul. 26, 2022     (NL) ..................................... 2032605

(51) Int. Cl.
*A61B 5/00*          (2006.01)
(52) U.S. Cl.
CPC .......... *A61B 5/6831* (2013.01); *A61B 5/6823* (2013.01); *A61B 2560/0468* (2013.01);
(Continued)

(58) Field of Classification Search
CPC ...... A61B 2503/045; A61B 2560/0468; A61B 2562/043; A61B 2562/164;
(Continued)

(56) References Cited

U.S. PATENT DOCUMENTS

2020/0015746 A1*   1/2020  Bambang Oetomo ......................
                                                        A61B 5/0816
2020/0146625 A1*   5/2020  Nousiainen .......... A61B 5/6831

FOREIGN PATENT DOCUMENTS

WO      WO-2008/092098 A2      7/2008
WO      WO-2022/031166 A2      2/2022

* cited by examiner

*Primary Examiner* — Scott Luan
(74) *Attorney, Agent, or Firm* — Quarles & Brady LLP

(57)                    ABSTRACT
The present invention relates to a defibrillation protected flexible sensor belt (1) suitable for being worn around an abdominal part of a human body. The belt comprises: electrodes (8) for contacting a skin of the body; a flex-PCB (10) carrying wiring (16) that connects the electrodes for readout, and a barrier (20) that encapsulates the wiring. The barrier includes: a primary barrier structure (21) formed by a dielectric carrier substrate of the flex-PCB and a dielectric cover layer that covers the wiring; and a secondary barrier structure that encapsulates the first barrier structure. The secondary barrier structure comprises: a first layer (22-1) comprising a first electrically insulating elastomeric composition (22-1*c*) that extends at least along a skin-facing side (25) of the belt, and a second layer (22-2) comprising a second electrically insulating elastomeric composition (22-2*c*) that extends along a non-skin facing side (26) of the belt.

16 Claims, 5 Drawing Sheets

(52) U.S. Cl.
CPC ... *A61B 2562/164* (2013.01); *A61B 2562/166*
(2013.01); *A61B 2562/227* (2013.01)

(58) Field of Classification Search
CPC ........ A61B 2562/166; A61B 2562/227; A61B
5/282; A61B 5/6823; A61B 5/6831
See application file for complete search history.

BABY VITAL SIGN MONITORING BELT

RELATED APPLICATIONS

This application is a 35 U.S.C. § 371 national phase application of PCT/NL2023/050399 (not yet published), filed on Jul. 25, 2023, entitled "BABY VITAL SIGN MONITORING BELT", which application claims the benefit of NL-2032605 filed Jul. 26, 2022, all of which are incorporated herein by reference in their entirety.

TECHNICAL FIELD AND BACKGROUND

The present disclosure relates to a flexible sensor belt that is configured to be worn around an abdominal part of a human body, in particular a neonate, especially a premature neonate.

The present disclosure is particularly concerned with medical aids for the nursing, caring and vitals monitoring, in particular in a clinical setting, of babies, e.g. neonates and premature neonates.

Preterm babies, i.e. babies that were born after a pregnancy of less than 37 weeks, are typically cared for by neonatal intensive care units (NICU) in hospitals, in isolation in an incubator while their vital signs are continuously monitored. Conventionally, such vital signs are monitored using conventional means for providing an electrocardiogram (ECG), such as to monitor their cardiac signal.

An ECG is commonly provided using adhesive electrodes adhered to the baby's body. Such electrodes are adhered to various parts of the body to detect different electrical physiological signals. Adhering of these electrodes is desired to ensure sufficient contact between the electrode and the skin, and to prevent accidental moving of the electrodes from their desired location on the body.

Although this method allows the baby's vital signs to be monitored in a reliable manner continuously, there are a number of disadvantages associated therewith. A main disadvantage is that such electrodes are generally not suitable for use during defibrillation. Further, adhering of electrodes to the skin of the premature baby itself is not desired because the skin of preterm babies is very sensitive. The use of adhesive electrodes is for that reason unpleasant and can even be even harmful. Removal of the electrodes hurts the baby, causing stress to the baby and/or his or her parents. Such removal occasionally may even damage the skin, causing small wounds and increasing the risk of infection. Taking into account that typically the electrodes are to be replaced every few days (e.g. every five days), it may be understood that this disadvantage is not negligible—in particular for babies that are to be monitored over a period of multiple weeks. Additionally, some conventional adhered electrodes may negatively affect or even damage a baby's skin during application of an external defibrillation pulse. A further disadvantage is the fact that conventional adhesive electrodes are wired, which may lead to entanglement of patient and/or user.

SUMMARY

The present application aims to address one or more of the above issues while at least maintaining wear comfort and/or minimizing potential skin damage, even upon prolonged wear.

Aspects of the present disclosure relate to a flexible sensor belt. The belt is suitable for being worn around an abdominal part of a human body, in particular a baby, e.g. a premature neonate.

As will be explained in further detail herein below the belt advantageously improves compatibility with general standards as to safety and performance of medical electrical (ME) equipment and ME systems, in particular electrocardiogramonitoring equipment. The belt is suited for application as a medical instrument in a medical setting such as an IC, including high-care, and medium-care units of a hospital.

Advantageously, the present disclosure addresses compatibility with required applicable standards for medical electrical (ME) equipment in combination with maintaining, or even improving, wear comfort, hygiene level, and minimizing potential skin damage, even upon prolonged wear.

The belt comprises an electrode portion having one or more electrodes with a surface for contacting with a skin of the body. When applied, the electrodes make contact with the skin of the baby. The electrodes receive electric physiological signals from the body of the baby, in particular from chest muscles, abdominal muscles, and from the heart of the baby from which vital signals such as respiratory signals and heart signals (like an ECG) may be obtained.

The belt further comprises a flexible printed circuit board (flex-PCB) carrying wiring. The wiring connects the one or more electrodes for readout. A barrier is provided that encapsulates and electrically shields the wiring.

The barrier includes a primary barrier structure and a secondary barrier structure. The primary barrier structure comprises, or is essentially formed by, a dielectric carrier substrate of the flex-PCB, and a dielectric cover layer that covers the wiring opposite the carrier substrate. The secondary barrier structure encapsulates the first barrier structure. Said secondary barrier structure comprises, or is essentially formed by: a first layer that comprises a first electrically insulating elastomeric composition and that extends at least along a skin-facing side of the belt; and a second layer that comprises a second electrically insulating elastomeric composition and that extends along a non-skin facing side. The first and second layer in combination encapsulate at least portions of the belt that supporting the electrical wiring. In some embodiments, the secondary barrier encapsulates the entire belt, including fitting portions. It will be understood that contact faces of the electrode remain accessible to contact the skin. To mitigate ingress of liquids, e.g. sweat, the layers are typically dense or at least non-porous.

In combination, the barrier structures are configured advantageously provide defibrillation proofing in combination with assuring an appropriate flexibility and geometry, in particular thickness, that allows safe and comfortable wear, even over prolonged periods.

The electrical insulation as provided by the combination of the primary and secondary barrier structures advantageously mitigates a potential electrical discharge to the skin. For example, when a condition or change in the vital signs of the baby is detected that requires application of electromagnetic stimulation (e.g. defibrillation). Providing the electrical insulation further advantageously mitigates dissipation of electrical discharge (e.g. defibrillation) away from body via circuitry comprised in the belt, e.g. the flex-PCB, even in case one or more electrode pads for defibrillation are positioned in close proximity or even overlap a portion of the belt. Accordingly, the belt as disclosed herein need not be removed (e.g. by medical staff) in case a defibrillation pulse is to be applied and can remain in a sensing position around the body, even when the defibrillation pads are positioned in close proximity to, or even in a position that partially overlap with the wiring of the belt. Mitigating a need to remove the belt prior to administration of a defibrillation pulse can improve an emergency response time, reduce stress to the patient, and/or reduced a delay in resumption of vital sign monitoring following administration of the pulse.

The flex-PCB and the barrier can have a comparatively lower overall thickness or higher flexibility, as compared to an insulation formed solely by a silicone rubber, or a barrier provided solely by the flex-PCB. Advantageously, a thickness of the belt, as defined by a combined thickness of the carrier substrate of the PCB and the remainder of the barrier structures, but excluding the electrodes and connectors, can be ≤5 mm. That is a combined thickness of the barrier and optional further cover layers does not exceed 5 mm. The thinner the belt the less the contact pressure imparted by the belt onto the skin of the patient can be. Advantageously, the combined thickness can be ≤2.1±0.15 mm.

As such the barrier as disclosed herein can be understood to contribute to providing a belt having an optimal balance in defibrillation proofing in combination with physical properties such as flexibility and robustness with a minimal thickness of the belt. As further detailed herein below the above advantages can be synergistically combined with one or more of softness, conformability, and/or mild adhesion to the skin, optionally in combination with improved hygiene, e.g. by mitigation collection of dirt/dust during use.

In a preferred embodiment, the first layer can be softer (have a lower hardness) than the second layer. Providing a softer layer along a skin-facing side of the belt can improve wear comfort and/or further reduce the contact pressure imparted onto the patient. Forming the opposing side with a comparatively harder composition can advantageously improve structural integrity and/or resilience of the belt as a whole, e.g. during application of the belt around the body.

In another or further preferred embodiment, the first layer can advantageously have a higher tack than the second layer. Forming the second layer, at least along portions for contacting with the skin, of a composition having a comparatively higher tack can advantageously mitigate inadvertent displacement of the electrodes during wear. Using a composition with a comparatively lower tack, preferably a non-sticky composition, along non-skin contact areas of the belt advantageously improves handleability and hygiene of the belt.

In a preferred embodiment, the first electrically insulating elastomeric composition having a hardness as defined by a Shore-A hardness below 10, preferably a hardness as defined by a Shore-00 hardness in a range of 30 to 50, and the second electrically insulating elastomeric composition is a flexible mold rubber composition having a hardness as defined by a Shore-A hardness in a range of 1 to 20.

Accordingly, in some preferred embodiments the first electrically insulating elastomeric composition can have a hardness that is lower and a tack that is higher than respective hardness and tack of the second electrically insulating elastomeric composition.

In a preferred embodiment, the first electrically insulating elastomeric composition and/or the second electrically insulating elastomeric composition can be flexible mold compositions, e.g. a rubber mold composition. Mold compositions can advantageously be applied using commonly available techniques.

Silicone-based mold rubber compositions having a hardness in the specified range were advantageously found to (additional to insulating barrier properties) provide a mild tack to, and easy removability from, the skin, respectively sufficient strength, elasticity, to maintain desired elasticity of the belt in combination with reduced-fouling properties.

It will be appreciated that in some embodiments the upper and lower layers of the secondary barrier can be made of a single composition or highly similar compositions, e.g. a composition having a Shore-A hardness in a range of about 0 to about 1 or a Shore-00 hardness in a range of about 40 to about 50. Forming the secondary barrier of a single composition can advantageously reduce manufacturing complexity.

In a preferred embodiment, the flexible sensor belt comprises a connector that is electrically connected to the one or more electrode via the wiring of flex-PCB for external readout and/or signal processing. Advantageously, the connector can be configured to transmit collected data wirelessly to a unit for processing, e.g. by a transceiver unit that is connected to the connector via a matching connector.

As such, the belt can be considered as a consumable, whereby data transmitters, readout electronics and/or data display(s) can be re-used and/or shared between a plurality of belt.

It will be understood that belt and in particular the skin contacting portions thereof are formed of medical grade materials.

To further minimize contamination of the belt during use areas of the belt layer the belt can be fully coated with a non-stick coating, with the exception of portions coated by the first layer, the connector, and the electrode surfaces.

To improve robustness of the belt and/or to prevent exposing the flex-PCB under stretched condition the flex-PCB can be provided with one or more anchoring points, such as cutouts or apertures that allow a direct contact between the first and the second electrically insulating composition (e.g. allowing the silicon composition to flow through the PCB to contact an opposing insulation layer. Preferably, the anchoring points are provided in close proximity of the one or more electrodes, e.g. between adjacent electrodes.

Advantageously the belt can have an overall stretchability that allows a positioning of the belt around the body with a snug, yet comfortable fit to the skin. A loose fit may risk displacements or even wrinkling of the belt, which can hurt the baby. Converse, an excessively tight fit may similarly cause discomfort, skin damage, or hinder or even obstruct chest expansion. To mitigate discomfort, skin damage, and/or potential hindrance the electrode portion of belt preferably has a stretchability (without loss of essential functionality) in a direction along a length of the belt of 5%-15%, preferably about 10%, when subjected to a tensile force of 5 Newton in the length direction. A remaining portion of the belt (outside the electrode portion) for extending around the abdominal part preferably has a stretchability in a direction along a length of the belt of at least 40%, preferably ≥50%, when subjected to a tensile force of 5 Newton in the length direction.

To control a stretchability of the belt the flex-PCB may be provided with a stiffener. The stiffener can reduce a stretchability of the belt, e.g. in portions that are outside a direct contact with the baby such as a tail holding the connector. Alternatively, or in addition, the stiffener can control a spread in separation distance between adjacent ones of the electrodes. In some embodiments, the flex-PCB comprises a meander structure. A meander structure can advantageously provide local increased flexibility and stretchability without loss of essential functionality. At the same time cutouts portions besides the meander can serve as anchoring points that allow contact between the first and the second layer.

According to a second aspect there is provided a system for monitoring the vital signs of a human, in particular a baby, comprising the belt according to the present disclosure and one or more an electronic unit configured for reading out, processing, and displaying and/or recording, a signal of the one or more sensor comprised in the belt.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
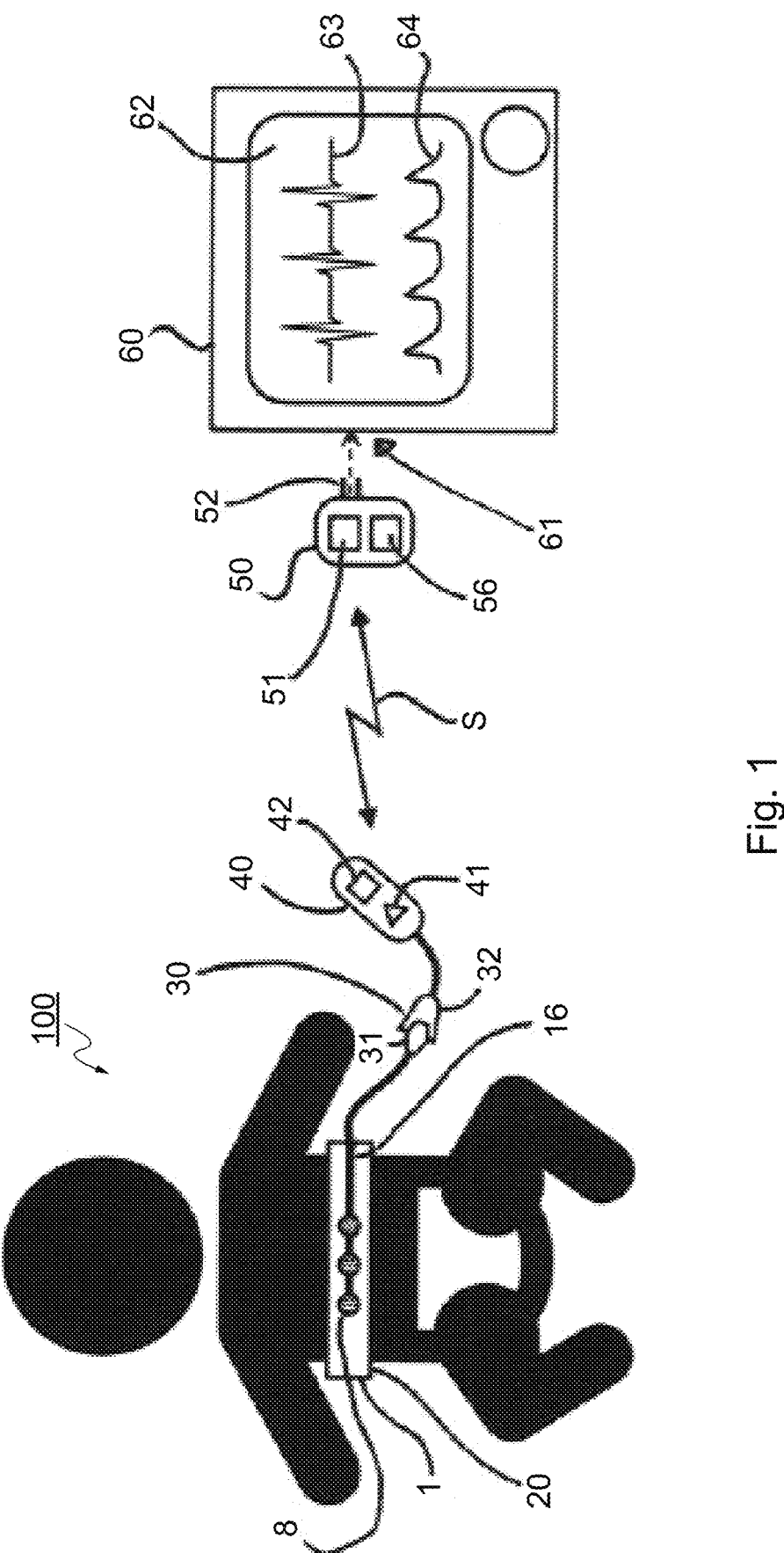
FIG. 1 schematically illustrates a monitoring system in accordance with an embodiment of the present invention.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise. As used herein a deviation indicated ± shall refer to a deviation of either side of the indicated value. For example, an indication of 3±1 shall refer to a range of 2-4.

As used herein terminology relating to dialectic qualities, electrically insulating qualities of layers/compositions and electrical is intended to reflect materials that fall in in the class on electrical insulators as opposed to conductors (e.g. metal) and semi-conductors. Insulators can be qualifies as materials an electrical conductivity less than 10-8 S/cm. Typically, used materials related to polymers having a dielectric constant $(\epsilon) \leq 5$ (@1 Mhz) preferably lower, e.g. below 4 or below 3 (e.g. rubbers).

The present invention, in accordance with a first aspect thereof, provides a flexible sensor belt that is suitable for being worn around an abdominal part of a human body, in particular a baby, especially a neonate. The belt comprises; an electrode portion 2 having one or more electrodes 8 with a surface 8s for contacting a skin of the body; a flexible printed circuit board 10 (flex-PCB) comprising wiring 16 that connects the one or more electrodes for readout; and a barrier 20 that encapsulates and electrically shields the wiring. The barrier 20 includes: a primary barrier structure 21 and a secondary barrier structure 22 that encapsulates the first barrier structure. The primary barrier structure 21 comprises or is essentially formed by a dielectric carrier substrate 10s of the flex-PCB 10 and a dielectric cover layer 10c that covers the wiring opposite the carrier substrate. The secondary barrier structure 22 comprises: a first layer 22-1 that extends at least along a skin-facing side 25 of that belt and that comprises or is essentially formed of a first electrically insulating elastomeric composition the belt, and a second layer 22-2 that extends along a non-skin facing side 26 of the belt and that comprises, or is essentially formed of, a second electrically insulating elastomeric composition.

Inventors found that suitable compositions may be selected by a characteristic Shore hardness values. Shore A hardness can be routinely determined according to ASTM D2240-15.

The adhesive properties of the first layer can be characterized by a probe tack energy value. The probe tack energy value of the first layer is preferably lower than that of the second layer. In a preferred embodiment, the first elastomeric composition has a probe tack energy value of at least 10 mJ/cm2 when tested on standard substrate maintaining a constant crosshead speed of 10+/−0.1 mm/s. (Tack energy values can be determined routinely for example as set out in ASTM2979). A minimum of 10 mJ/cm2 was found to provide sufficient adhesion to mitigate electrode displacement. Higher values are possible, e.g. up to 100 or 500 mJ/cm². An upper limit can be defined by a value at which removal of the belt starts to cause discomfort to the baby.

To prevent discomfort or potential skin damage upon the first layer electrically insulating elastomeric composition can be selected to have a peel adhesion value below about 3 N/mm (±10%) when peeled from a standard substrate (e.g stainless steel) as determined by ASTM 3330. Preferably, the peel-off value is ≤2 N/mm, e.g. 0.1-2 N/mm (±10%).

A thickness and resistivity of the barrier, e.g. each of the respective layers, is preferably such that the barrier can fully withstand, without breakdown, external electrical discharges, e.g. from defibrillation pads. Inventors found that the belt comprising a reinforced insulation can advantageously be in compliance with electrical safety and performance standards according to one or more of IEC 60601-1, IEC 60601-2-27, and ANSI/AAMI EC12.

Inventors confirmed that the belt can withstand, without breakdown, application of a one second (±10%) application of 5000V DC (±10%); and a one min (±20%) application of 1000 Vrms (±10%) as applied between two of the one or more electrodes; and opposing faces of the insulation at the skin-facing and the non-skin facing side of the belt.

Defibrillation protective qualities depend largely on a thickness and resistivity of first and second barrier layers, i.e. the dielectric carrier substrate, the dielectric cover layer and the first and second layers of first pf the second barrier structure as provided on either side of the first barrier structure. In practice relevant thickness of a given material selection can be determined experimentally with a routine electrical breakdown setup.

The first and the second electrically insulating composition can be silicone-based. For example, one or more of the first and second layer can be provided by liquid precursor composition that can be hardened (e.g. cross-linked) after application. In contrast to textile based layers silicone rubbers offer improved cleanability and reduced slip of the belt while applied along skin.

The belt generally has a longitudinal shape with a length that is very long in comparison to a width and thickness of the belt. The length depends on a size of the body the belt is intended for. To accommodate for different babies the belt can be provided in a number of variants with a length for fitting with babies within one or more size categories. Typically the length of the belt is between 500-900 mm. Advantageously the weight of the belt can be less than 30 grams (including Belt Connector).

The number of electrodes depends on the intended application. For vital sign monitoring (e.g. ECG and/or respiratory function) the electrode section typically includes at least three electrodes including a first, a second electrode, and a reference electrode that are spaced in a longitudinal direction over the belt. The area between the electrodes and up to 20 mm besides a hart line of the outermost most electrodes is referred to as the electrode portion. Of course the belt can be fitted with a different number of electrodes or different sensors such as a temperature sensor.

The electrode portion and at least a fitting portion extending towards a first terminal end of the belt are generally wrapped around the body of the patient. The belt generally also includes a so-called tail section extending to a second terminal end of the belt (opposite the first). The tail section generally comprises means, e.g. holes, that cooperate with a matching means at the fitting portion to fit the belt around the body (e.g. torso). A remaining portion of the tail can comprise a connector for readout of electrode signal(s). This portion generally remains free during use (not wrapped around the body). Because the belt is elastic, stretchable, a snug, yet comfortable fit around a part of the body (e.g. abdomen of the baby) may be realized. It will be appreciated that the belt can be provided in a number of different sizes, e.g. lengths tuned in accordance with a size category of the baby.

FIG. 1 schematically illustrates a monitoring system comprising a belt 1 in accordance with an embodiment of the present invention. The system comprises a wearable device 1, embodied as a belt to be worn around an abdominal part of the body 100 of a preterm baby. It is not essential that the wearable device is embodied as a belt 1, and in principle the wearable device 1 may be embodied differently, for example as a harness. The wearable device in accordance with the invention includes or provides a carrier, here the belt 1, to the electrodes and other components.

Hereafter, it will be assumed that the wearable device is embodied as a belt, and that the belt itself is the carrier. Therefore, the terms 'carrier' and 'belt' may sometimes have been interchanged in the text and be referred to by the same reference numeral.

The belt comprises a plurality of electrodes 8 that make contact with the skin of the baby 100. The electrodes 8 receive electric physiological signals from the body 100 of the baby, in particular from the muscles from which the respiratory signal may be obtained, and from the heart of the baby. The system further comprises one or more electronic units configured for reading out, processing, and displaying and/or recording, electric physiological signals from the one or more sensor comprised in the belt.

The belt is connected to a sensor unit 40. This unit receives the electric physiological signals from the electrodes 8, and amplifies these using amplifier circuitry 41. The sensor unit 40, from the signals received from the electrodes 8, generates a sensor signal. The sensor signal is transmitted to a receiver unit 50, which processes the signal, and provided to a monitor unit 60 for presentation on a display 62.

The sensor signals from the sensor unit 40 will be transmitted wirelessly, via wireless signal S, to the receiver unit 50. To this end, the sensor unit 40 comprises a data communication unit 42. Similarly, the receiver unit 50 likewise comprises a data communication unit 56. For example, the communication units 40 and 50, may be configured for enabling data communication via Bluetooth low energy. However, alternative data communication protocols may likewise be applied by the units 42 and 56. The receiver unit 40 further comprises a processor 51 that is configured for processing the sensor signals and provide vital signs signals to the monitor 60. The processor may apply certain algorithms that are stored in a memory of the receiver module to perform this task.

The receiver unit 50 is connected to that monitor 60 using a third connector 52 which is received in a cradle or fourth connector 61 in the monitor unit 60. As mentioned herein before, dependent on the embodiment, the receiver unit may be connected in a different way to the monitor 60. For example, the receiver unit 50 may have a wired connection and a plug that connects to a socket in the monitor 60. The receiver unit 50 may alternatively apply wireless communication to the monitor 60 in yet a different embodiment, without departing from the present invention. Also, in a preferred embodiment, receiver unit 50 may be integrated into the monitor 60, e.g. via the cradle 61.

The monitor 60 comprises a display 62 in which the vital sign signals are presented, for example to the medical staff. For example, the monitor unit 60 may present an ECG signal 63 and a respiratory signal 64.

The connection between the belt 1 and the sensor unit 40 is provided via a connector assembly 30. The connector assembly consists of a first connector 31 and a second connector 32 that are complementary to each other, in the sense that they are cooperatively shaped to enable a tight mechanical and electrical connection. The electric physiological signals from the electrodes 8 are provided to the first connector via a conductive path. As seen more clearly in FIGS. 2, 5, and 7, the conductive path is provided by an electric circuit, wiring 16, carried or provided by the flex-PCB 10. The flex PCB includes a carrier substrate 10s that is sufficiently flexible for the flexible belt. The carrier substrate is typically formed by a flexible plastic substrate. The substrate can e.g. be polyimide, polyether ether ketone (PEEK) or polyester film. In a preferred embodiment, the carrier substrate is formed by polyimide (e.g. as commercially available under the name Kapton®—DuPont). A dielectric cover layer 10c covers the wiring opposite the carrier substrate. The dielectric cover layer comprises, or is essentially formed of, a plastic dielectric composition. The composition can be similar or the same as the carrier substrate, E.g. polyimide, PEEK or polyester. The cover layer preferably has a thickness ≤70 μm. Typically in a range between 20 and 70 μm, e.g. about 25-45 μm. Thicker layers would negatively affect belt flexibility and/or stretchability and thus wearer comfort. The flex-PCB as a whole, including carrier, wiring, cover layer and optional adhesive layers preferably has a thickness ≤500 μm, typically 225-500 μm, e.g. 285±50 μm.

Figure 2:
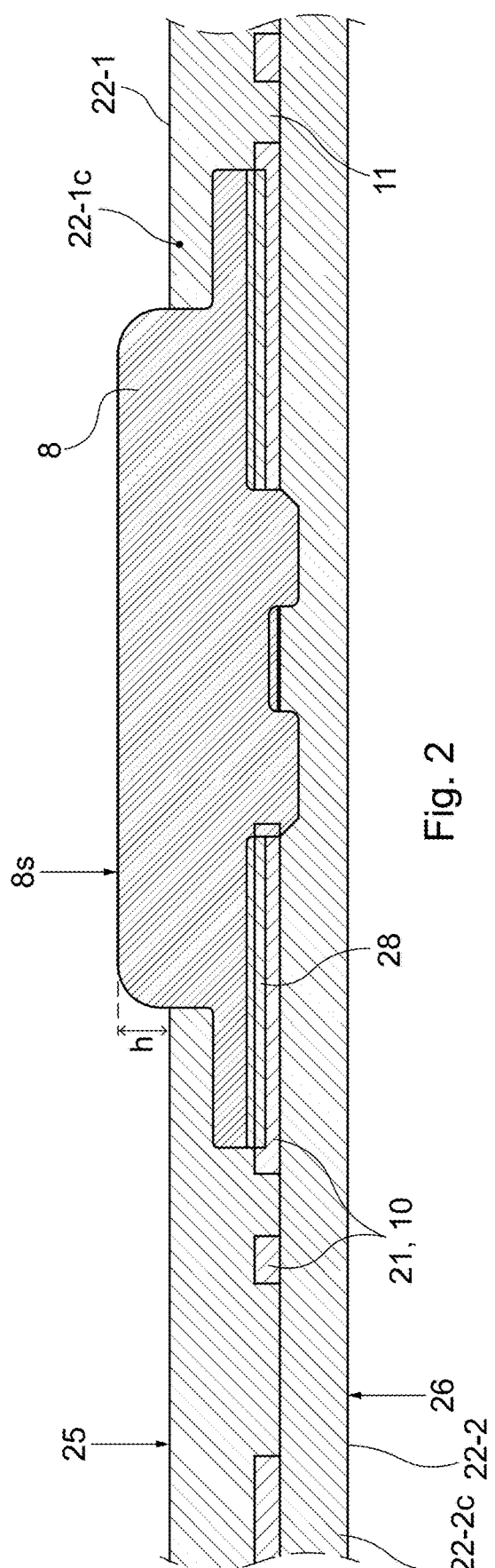
FIG. 2 schematically illustrates a partial cross-section side view of embodiment of the present invention.
Figure 6:
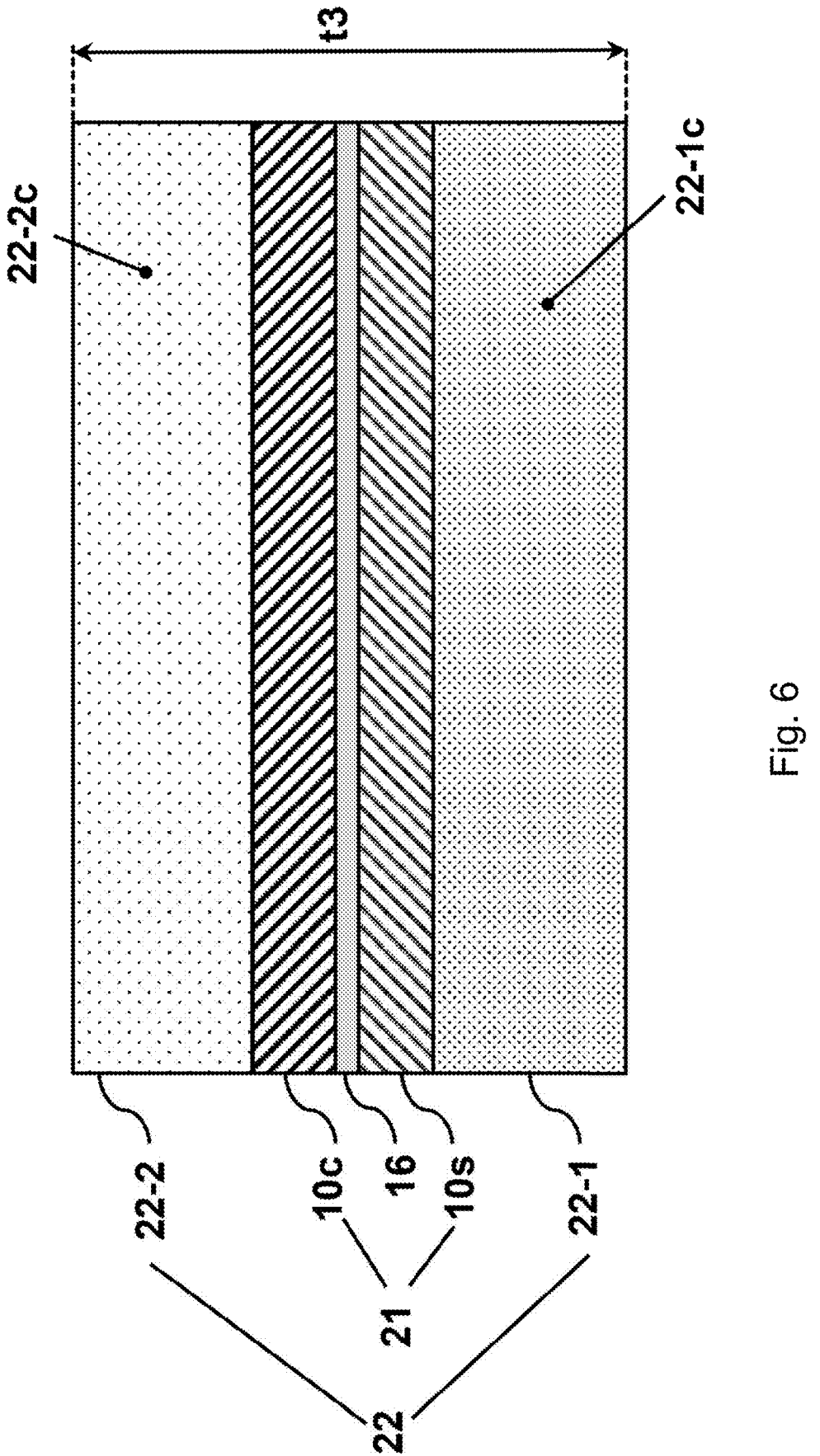
Figure 7:
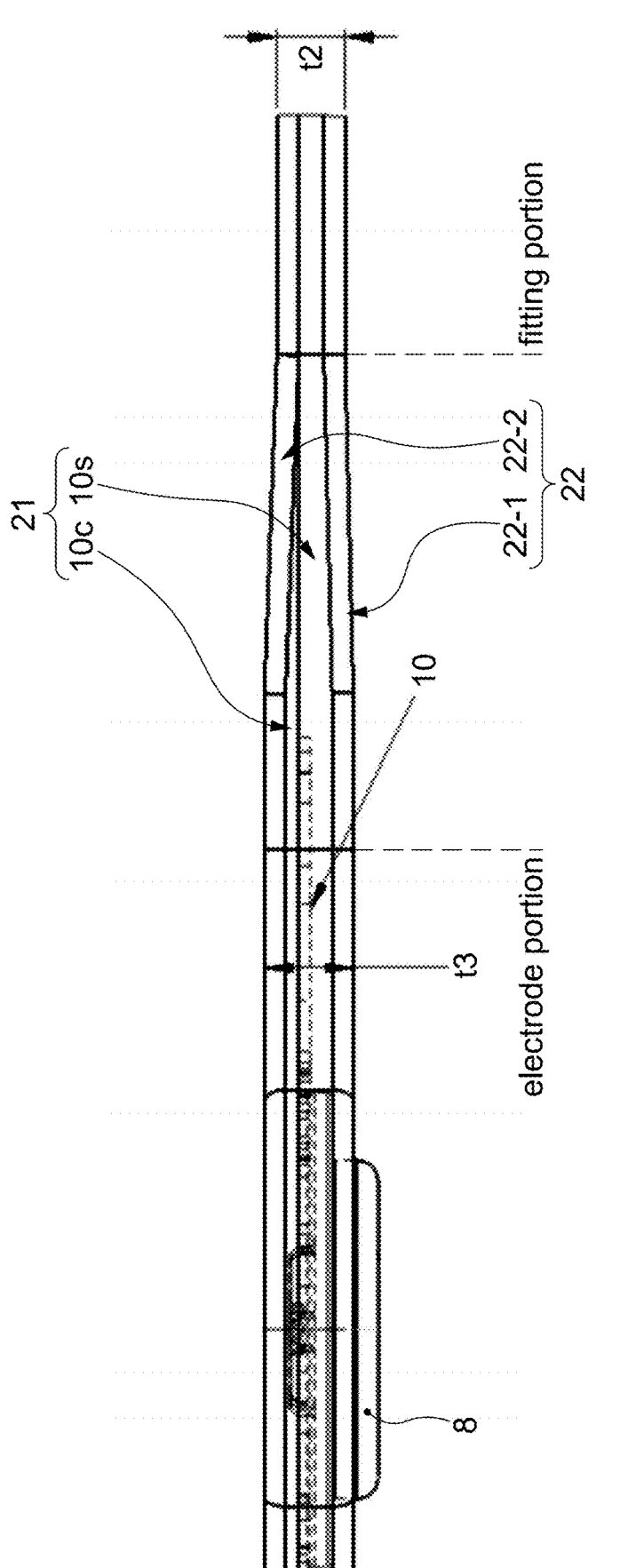

FIG. 2 provides a schematic partial a cross-section side view of an embodiment of the present invention at the electrode portion. The electrode 8 is mounted on a flex-PCB 10. As best seen in FIGS. 6-7, the flex-PCB includes the wiring for readout and a dielectric cover layer 10c that covers the wiring opposite the carrier substrate 10s. Together the substrate 10s and cover 10c provide a first barrier structure 21 that encapsulates the wiring 10. The belt is further provided with a secondary barrier structure 22 that encapsulates the first barrier structure 22. The barrier properties offered by the comparatively thin primary barrier structure are thus supplemented by the secondary barrier structure, which at the same time improves wearer comfort while enabling flexibility and stretchability.

It will be understood that the surface 8s of the electrodes for contacting the skin is left free. Typically the electrodes protrude from the insulation by a small distance 'h'. The smaller the protrusion the smaller the pressure that is imparted onto the skin. The contact surface 8s of the electrodes shall preferably elevate from the internal side of the belt by about 0.60±0.40 mm.

As indicated in FIGS. 2, and 5 to 7 the secondary barrier structure 22 comprises an upper layer, also referred to as the first layer 22-1, and a lower layer, also referred to as the second layer 22-2. During use the first layer 22-1 can define a skin-facing side 25 of the belt (at the patient side). The second layer 22-2 can form a non-skin facing side 26 of the belt (away from the patient).

The secondary barrier can be provided by overmoulding, e.g overmoulding with a suitable first and second electrically insulating elastomeric composition 22-1c, 22-2c.

The barrier protects the patient and system from electrical pulses such as imparted onto the body during a defibrillation event. The carrier substrate 10c of the flex PCB can span an entire length of the belt (from end to end). In some embodiments the PCB can be limited to a longitudinal section of the belt spanning from the electrode portion to the connector 31. Optionally or additionally, the belt can comprise a support layer that carries the PCB and/or the secondary barrier structure, in particular for sections without PCB such as a fitting portion. As indicated in FIG. 7 the carrier substrate 10c can extend from the electrode portion into the fitting portion of the belt to serve as carrier for the secondary barrier structure.

Layer 28 is a conductive layer, typically comprising a conductive adhesive, that allows to connect the electrodes 8 to the circuitry of the PCB. A conductive glue or bond may be used in layer 28 to adhere the electrodes 8 to the electronic circuit and the PCB. The glue may be a cyanoacrylate or a two-part conductive epoxy, although the skilled person will recognize suitable alternatives.

In a preferred embodiment, the flex-PCB comprises a meander structure and/or one or more cutouts 11 or anchors. The meander can provide stretchability. The cutouts, anchors, or apertures besides the meander that can fill-up with insulation during, e.g. during overmoulding (the first layer 22-1 and/or second layer 22-2) and prevent exposing the PCB when the belt is under stretched condition.

Figure 3:
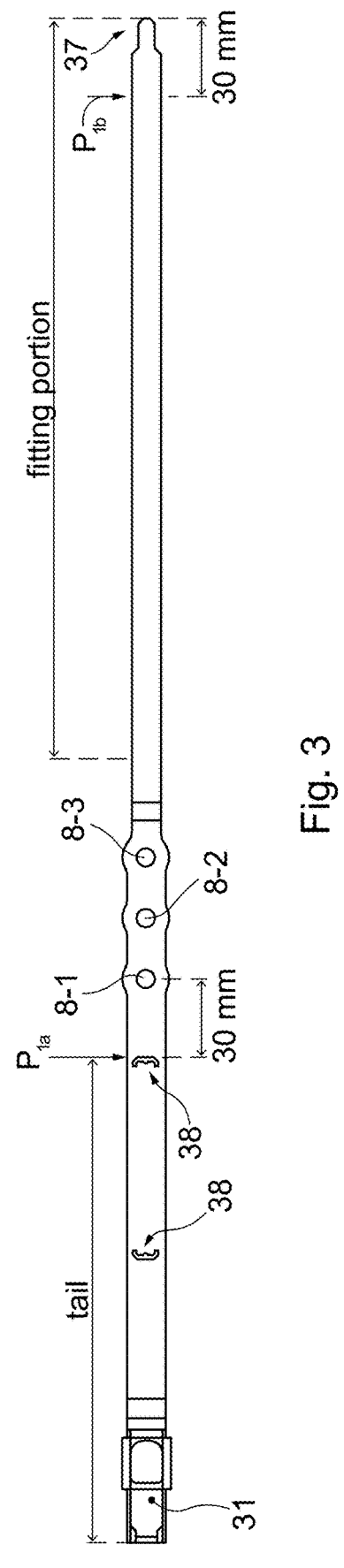
FIG. 3 schematically illustrates plan view of an embodiment of the present invention.
Figures 4, 5:
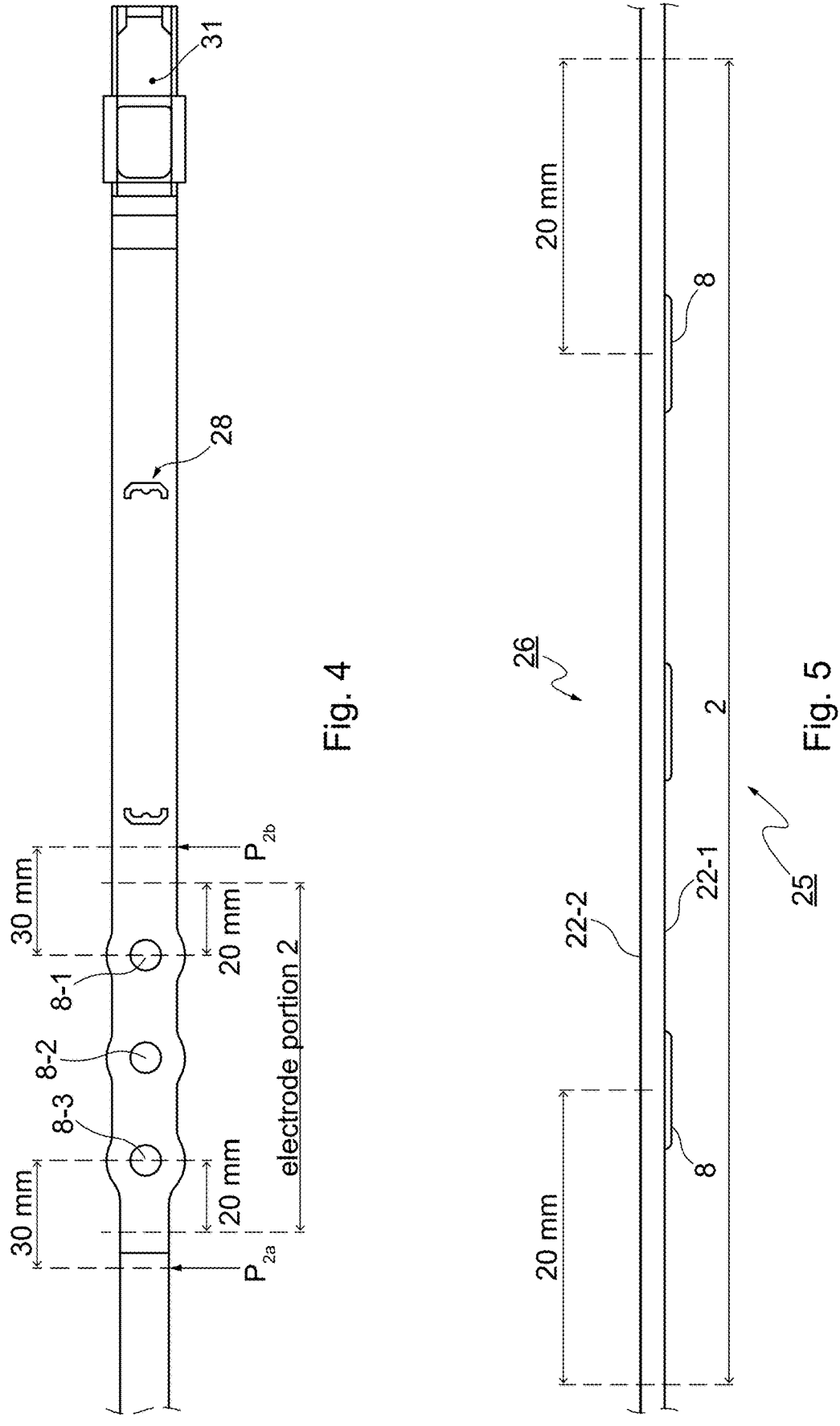
FIG. 4 schematically illustrates a partial plan view of an embodiment of the present invention.
FIGS. 5, 6 and 7 schematically illustrate partial cross-section side views of embodiments of the present invention.

FIG. 3 schematically provides a plan view of an embodiment of the present invention. FIG. 4 schematically illustrates a partial plan view of the embodiment. The embodiment comprises three electrodes 8-1,8-2,8-3 that are disposed along the electrode portion 2 of the belt. Extending from the electrode portion 2 towards a first terminal end is the so-called tail portion. The tail portion includes a connector 31 that is functionally connected to the electrodes via the flex-PCB for read out. Extending towards an opposite terminal end is a fitting portion for the belt for wrapping around the patient's body. The fitting portion includes a fitting connector (e.g. lip 37) for cooperating with a corresponding fitting connector (e.g. slot 38) along the tail. The remaining portion of the tail can be free (not in wrapped around the body).

The belt can advantageously provide an elongation in length of at least 50% (length under stress (Ls) divided by the length in rest (L0)≥1.5), if subjected to a tensile force of 5 Newton in the length direction. Force shall be applied on the entire length of the belt not taking in account the tail region (as measured between camping positions P1a (30 mm from a terminal end of the fitting portion) and P1b (the mm from a heart-line of the electrode nearest the tail).

The belt can provide an elongation in length of at least 10% (Ls/L0≥1.1) in the electrode portion, if subjected to a tensile force of 5 Newton in the length direction. (As measured between camping positions P2a and P2b (see FIG. 4).

FIGS. 5, 6, and 7 schematically illustrate partial cross-section side views of embodiments of the present invention. FIG. 5 illustrates an electrode portion 2 of the belt, including three electrodes, a first layer 21 and a second layer 22 and their position relative to a person's skin during an intended use. FIG. 6 provides a detail cross-section side view of a belt section between two adjacent electrodes. FIG. 7 illustrates a transition section of a belt between the electrode region (left in figure) and a fitting portion (right in figure).

The barrier 20 as formed by primary and secondary barrier structures 21,22 preferably encapsulates the entire belt, excluding the protruding portions with skin-facing surface of the electrodes surface 8 and the connector 31. The first layer 22-1 is preferably restricted to skin facing portions of the belt, typically the patient side of the electrode portion 2 and at least part of a skin facing side of the fitting portion up to fitting connector. The remainder of the belt (excluding electrodes and connector is preferably covered) by a non-stick layer. It will be appreciated that the non-stick coat may be provided by the second layer 22-1. Alternatively, the non-stick coat may be provided by one or more additional layer of a further composition different than the first and the second.

To avoid pressure points/lines along the skin of the patient the belt shall preferably have no sharp edges or corners, e.g. rounded corners/edges.

As mentioned, the support layer 10s of the PCB may, in some embodiments, extend along the entire length of the belt between the opposing ends at the electrical and fitting connectors 31,37. In some embodiments the PCB may extend exclusively along the electrode portion 2 and the tail portion of the belt, e.g. up to electrical connector 31. In some embodiments the belt may include an elastic carrier layer. The elastic carrier layer can extend along the fitting portion an optionally one or more of the tail portion, and/or the electrode portion. The plastic carrier can provide stability, e.g. as an anchoring layer, during manufacturing. Additionally the carrier can provide further shielding between wiring, circuitry, and a patient's skin when positioned between the circuitry and a skin facing side of the belt.

A thickness of the belt (t3) excluding the electrical components (electrode) shall preferably not exceed 2.1±0.15 mm. A combined thickness of the first and second layers of the electrically insulating elastomeric compositions is, for silicone based rubbers or materials having similar resistivity, generally in a range of least 1.5 mm, typically at least 1.7 mm, up to about 1.9 mm, up to a practical maximum of about 4.8 mm. Thicker layers are possible from an electrical point of view but less preferably from one or more of wearer comfort, stretchability, and/or potential compliance with secondary devices, e.g. defibrillator bond pads. The thickness is generally equally (e.g. in range of 40/60 up to 60/40) distributed between the first and second layers.

A thickness (t2) of the belt at the fitting portions, including the optional elastic carrier, shall preferably not exceed 1.6±0.15 mm.

Inventors found that the belt according to the disclosure can advantageously comply with medical standard including IEC 60601-1 and IEC 60601-2-27.

For the purpose of clarity and a concise description, features are described herein as part of the same or separate embodiments, however, it will be appreciated that the scope of the invention may include embodiments having combinations of all or some of the features described. For example, while embodiments were shown for a belt comprising three electrodes, also alternative ways may be envisaged by those skilled in the art having the benefit of the present disclosure for achieving a similar function and result. E.g. the electrodes may be combined or split up into one or more alternative components e.g. two belts). The various elements of the embodiments as discussed and shown offer certain advantages, such as defibrillation proofing. Of course, it is to be appreciated that any one of the above embodiments or processes may be combined with one or more other embodiments or processes to provide even further improvements in finding and matching designs and advantages. It is appreciated that this disclosure offers particular advantages to monitoring of vital signs of babies with improved defibration proofing while maintaining advantageous aspects such as skin friendliness, reduced skin damage and/or general wearing comfort, and in general can be applied for any application benefiting from prolonged gentle yet stable skin-sensor contact with improved tolerance to application of external electrical pulses.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A flexible sensor belt suitable for being worn around an abdominal part of a human body, comprising:
an electrode portion having one or more electrodes with a surface for contacting a skin of the body,
a flexible printed circuit board (flex-PCB) carrying wiring that connects the one or more electrodes for readout, and
a barrier that encapsulates the wiring

12 wherein the barrier includes:
a primary barrier structure formed by a dielectric carrier substrate of the flex-PCB and a dielectric cover layer that covers the wiring opposite the carrier substrate; and
a secondary barrier structure that encapsulates the primary barrier structure, said secondary barrier structure comprising at least:
a first layer comprising a first electrically insulating elastomeric composition and that extends at least along a skin-facing side of the belt, and
a second layer, in addition to the first layer, comprising a second electrically insulating elastomeric composition and that extends along a non-skin facing side of the belt.

2. The flexible sensor belt according to claim 1, wherein the belt has a thickness≤5 mm.

3. The flexible sensor belt according to claim 1, wherein the first and the second electrically insulating elastomeric composition are silicone based rubber compositions.

4. The flexible sensor belt according to claim 1, wherein the first electrically insulating elastomeric composition is a cured flexible mold rubber based composition having a hardness as defined by a Shore-A hardness below 10, and
wherein the second electrically insulating elastomeric composition is a cured flexible mold rubber based composition having a hardness as defined by a Shore-A hardness in a range of 1 to 20.

5. The flexible sensor belt according to claim 1, wherein the first electrically insulating elastomeric composition, at least along portions for contacting with the skin of the body, has a hardness that is lower and a tack that is higher than the second electrically insulating elastomeric composition.

6. The flexible sensor belt according to claim 1, wherein the first electrically insulating elastomeric composition has a probe tack energy value ≥than 10 mJ/cm$^2$ when tested on standard substrate maintaining a constant crosshead speed of 10+/−0.1 mm/s.

7. The flexible sensor belt according to claim 1, wherein the first electrically insulating elastomeric composition has a peel adhesion when peeled from a standard substrate within a range of 0.1-2 N/mm as determined by ASTM 3330.

8. The flexible sensor belt according to claim 1, wherein the barrier is configured to withstand, without breakdown:
a one second (±10%) application of 5000V DC (±10%); and
a one min (±20%) application of 1000 Vrms (±10%) in accordance with ANSI/AAMI EC12.

9. The flexible sensor belt according to claim 1, wherein the first and the second electrically insulating elastomeric composition are silicone based.

10. The flexible sensor belt according to claim 1, wherein the flex-PCB is provided with one or more cutouts that allow a direct contact between the first and the second electrically insulating elastomeric composition.

11. The flexible sensor belt according to claim 1, wherein the electrode portion of belt has stretchability in a direction along a length of the belt of 5%-15%, when subjected to a tensile force of 5 Newton in a length direction.

12. The flexible sensor belt according to claim 1, wherein a remaining portion of the belt (3) for extending around the abdominal part, outside the electrode portion, has a stretchability in a direction along a length of the belt of at least 40%, when subjected to a tensile force of 5 Newton in a length direction.

13. The flexible sensor belt according to claim 1, wherein the flex-PCB comprises a meander structure.

14. The flexible sensor belt according to claim 1, further comprising a non-stick cover layer that extends along an exterior face of the barrier, except portions that are covered by the first electrically insulating elastomeric composition.

15. The flexible sensor belt according to claim 1, wherein the belt is connected to a connector that is electrically connected to the one or more electrodes via the wiring, said connector configured for wireless transmitting output data from the electrodes for external signal processing.

16. A system for monitoring vital signs of a human, comprising the belt according to claim 1 and one or more electronic units configured for processing a signal of the one or more sensors comprised in the belt.

* * * * *